(12) United States Patent
Iasemidis et al.

(10) Patent No.: US 9,730,628 B2
(45) Date of Patent: Aug. 15, 2017

(54) SYSTEM AND METHOD FOR IDENTIFYING A FOCAL AREA OF ABNORMAL NETWORK INTERACTIONS IN THE BRAIN

(71) Applicants: THE CLEVELAND CLINIC FOUNDATION, Cleveland, OH (US); Louisiana Tech University Research Foundation, Ruston, LA (US)

(72) Inventors: Leonidas D. Iasemidis, Choudrant, LA (US); Ioannis Vlachos, Ruston, LA (US); Balu Krishnan, Parma, OH (US); Andreas Alexopoulos, Moreland Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 766 days.

(21) Appl. No.: 14/203,742

(22) Filed: Mar. 11, 2014

(65) Prior Publication Data
US 2014/0276187 A1 Sep. 18, 2014

Related U.S. Application Data

(60) Provisional application No. 61/777,712, filed on Mar. 12, 2013.

(51) Int. Cl.
*A61B 5/04* (2006.01)
*A61B 5/05* (2006.01)
(Continued)

(52) U.S. Cl.
CPC ........ *A61B 5/4076* (2013.01); *A61B 5/04008* (2013.01); *A61B 5/0476* (2013.01);
(Continued)

(58) Field of Classification Search
CPC .... A61B 5/0476; A61B 5/4094; A61B 5/4076
See application file for complete search history.

(56) References Cited

U.S. PATENT DOCUMENTS 7,461,045 B1 12/2008 Chaovalitwongse et al.
2003/0093004 A1* 5/2003 Sosa ................. A61B 5/04
600/544
(Continued)

FOREIGN PATENT DOCUMENTS

WO 2013142051 A1 9/2013

OTHER PUBLICATIONS

Brito et al. Asymptotic Behavior of Generalized Partial Directed Coherence. Conf Proc IEEE Eng Med Biol Soc. 2010;2010:1718-21. doi: 10.1109/IEMBS.2010.5626856.*
Blinowska. Review of the methods of determination of directed connectivity from multichannel data. Med Biol Eng Comput (2011) 49: 521-529.*
(Continued)

*Primary Examiner* — Christian Jang
(74) *Attorney, Agent, or Firm* — Tarolli, Sundheim, Covell & Tummino LLP

(57) ABSTRACT

One aspect of the present disclosure relates to a system that can identify a focal area of abnormal brain interactions in a subject. Time series data can be received that corresponds to recordings from a plurality of regions in a brain of the subject during a resting period. Based on the time series data, an information inflow associated with each of the plurality of regions can be determined. The focal area of the abnormal brain interactions can be identified as one of the plurality of regions having a maximum information inflow.

17 Claims, 13 Drawing Sheets

(51) Int. Cl.
*A61B 5/00* (2006.01)
*A61B 5/0476* (2006.01)
*A61B 5/055* (2006.01)
*A61B 5/16* (2006.01)

(52) U.S. Cl.
CPC .......... *A61B 5/4094* (2013.01); *A61B 5/7246* (2013.01); *A61B 5/7271* (2013.01); *A61B 5/055* (2013.01); *A61B 5/16* (2013.01)

(56) References Cited

U.S. PATENT DOCUMENTS

| | | | |
|---|---|---|---|
| 2007/0066915 A1* | 3/2007 | Frei | A61B 5/048 600/544 |
| 2009/0216146 A1 | 8/2009 | Teicher et al. | |
| 2010/0049482 A1 | 2/2010 | He et al. | |
| 2010/0286747 A1 | 11/2010 | Sabesan et al. | |
| 2013/0096408 A1 | 4/2013 | He et al. | |

OTHER PUBLICATIONS

Schelter et al., "Assessing the Strength of Directed Influences Among Neural Signals Using Renormalized Partial Directed Coherence", Journal of Neuroscience Methods, 2009, vol. 179, pp. 121-130.

Baccala et al., "Generalized Partial Directed Coherence", Digital Signal Processing, Jul. 2007, pp. 163-166.

Prasanna, "Directional Information Flow and Applications", Aug. 2011, Arizona State University, pp. i-75.

Tana et al., "Exploring Brain Networks in Temporal Lobe Epilepsy by Using dDTF Analysis of fMRI Data", International IEEE EMBS Conference on Neural Engineering, Apr. 2009, pp. 550-553.

Varotto et al., "Partial Directed Coherence Estimated on Stereo-EEG Signals in Patients with Taylor's Type Focal Cortical Dysplasia" International Conference of the IEEE EMBS Buenos Aires, Aug. 2010, pp. 4646-4649.

International Search Report and Written Opinion on PCT/US2014/023010, mailed Jun. 12, 2014, pp. 1-14.

* cited by examiner

SYSTEM AND METHOD FOR IDENTIFYING A FOCAL AREA OF ABNORMAL NETWORK INTERACTIONS IN THE BRAIN

RELATED APPLICATIONS

This application claims the benefit of U.S. Provisional Application No. 61/777,712, filed Mar. 12, 2013, entitled "Method for Localizing the Epileptogenic Focus from Interictal Brain Signal Processing," the entirety of which is hereby incorporated by reference for all purposes.

TECHNICAL FIELD

The present disclosure relates generally to identifying a focal area of abnormal brain interactions and, more specifically, to systems and methods that can identify a focal area of abnormal brain interactions from time series data recorded during a resting period.

BACKGROUND

Epilepsy is among the most common disorders of the nervous system, affecting 1-2% of the world's population. It is a unique paroxysmal disorder characterized by chronically recurrent disruptions of the brain's normal activity (seizures), resulting from excessive electrical discharges of abnormal groups of neurons (the epileptogenic focus). The poor quality of life and psychosocial functioning associated with epilepsy exacts an enormous toll on patients and their families. Epilepsy has a substantial impact on society because patients lose employment potential while incurring high bills for their medical care.

Despite many decades of research and the development of new antiepileptic drugs, a large number (30-40%) of patients suffer from inadequately controlled seizures or undesirable side effects from their medication. For these patients, seizures can be controlled by surgical treatment (e.g., resective epilepsy surgery) and/or neuromodulation (e.g., targeted electrical stimulation). However, these treatments are only effective in patients in which the epileptogenic focus can be localized with a high degree of confidence. Neuro-recording methods (e.g., long-term electroencephalographic (EEG) recordings, magnetic resonance imaging (MRI), positron emission tomography (PET), subtraction ictal single photon emission computed tomography (SPECT) co-registered with MRI (SISCOM), and magnetoencephalography (MEG)) can be used to identify the epileptogenic focus; however, such neuro-recording studies are often inconclusive or negative since seizures typically occur unpredictably and without a warning, and interictal periods may not exhibit abnormalities (e.g., interictal spikes).

SUMMARY

The present disclosure relates generally to identifying a focal area of abnormal brain interactions and, more specifically, to systems and methods that can identify a focal area of abnormal brain interactions from time series data recorded during a resting period.

In one aspect, the present disclosure can include a system that identifies a focal area of abnormal brain interactions in a subject. The system can include a non-transitory memory storing computer-executable instructions and a processor that executes the computer-executable instructions to at least: receive time series data from a plurality of regions in a brain of the subject recorded during a resting period; determine an information inflow associated with each of the plurality of regions based on the time series data; and identify the focal area of the abnormal brain interactions as one of the plurality of regions having a maximum information inflow.

In another aspect, the present disclosure can include a method for identifying a focal area of abnormal brain interactions in a subject. The method can include steps that can be performed by a system that includes a processor. The steps can include: receiving time series data from a plurality of regions in a brain of the subject recorded during a resting period; determining an information inflow corresponding to each of the plurality of regions based on the time series data; comparing, by the system, the information inflow corresponding to each of the plurality of regions; and identifying the focal area as one of the identified regions exhibiting a maximum information inflow.

In a further aspect, the present disclosure can include a method for diagnosing a neurological disorder characterized by one or more focal areas of abnormal brain interactions in a subject. The method can include steps that can be performed by a system that includes a processor. The steps can include: receiving time series data from a plurality of regions in the brain of the subject recorded during a resting period; determining an information inflow corresponding to each of the plurality of regions; comparing the information inflow associated with each of the regions to determine the presence of one or more focal areas exhibiting a maximum information inflow; and diagnosing the neurological disorder based on the presence of one or more focal areas.

In another aspect, the present disclosure can include a system for diagnosing a neurological disorder characterized by one or more focal areas of abnormal brain interactions in a subject. The system can include a non-transitory memory storing computer-executable instructions and a processor that executes the computer-executable instructions to at least: receive time series data from a plurality of regions in the brain of the subject recorded during a resting period; determine an information inflow corresponding to each of the plurality of regions; compare the information inflow associated with each of the regions to determine the presence of one or more focal areas exhibiting a maximum information inflow; and diagnose the neurological disorder based on the presence of one or more focal areas.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
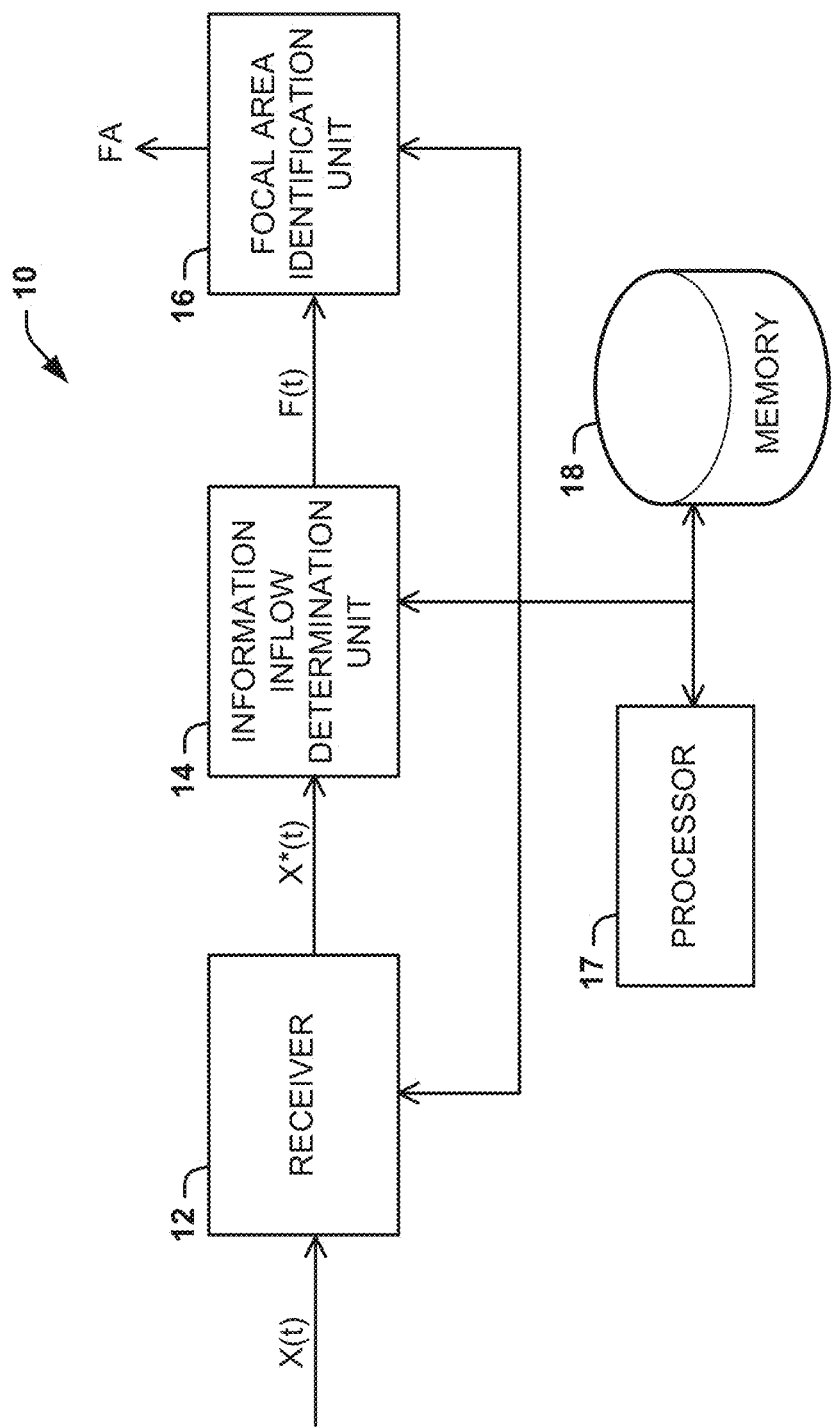
FIG. 1 is a schematic block diagram showing a system that can identify a focal area of abnormal brain interactions in a subject in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "focal area" can refer to an area of the brain (or "hot spot") where abnormal brain interactions are initiated or localized. The term "focal area" can include a single focal area, bifocal areas (e.g., two focal areas), or multifocal areas (e.g., more than two focal areas).

As used herein, the term "brain interactions" can refer to bidirectional relations between one or more electrical potentials, magnetic field potentials, and/or currents generated by one or more regions of the brain and detectable by a neuro-recording modality. In an example, the brain interactions can be abnormal brain interactions between regions of the brain that can be indicative of abnormal brain activity. The terms "abnormal brain interactions" and "abnormal network interactions in the brain" can be used interchangeably herein.

As used herein, the term "neurological disorder" can refer to a disorder of the nervous system characterized by abnormal brain activity. Examples of neurological disorders include, but are not limited to, paroxysmal neurological disorders (e.g., epilepsy, multiple sclerosis, encephalitis, traumatic brain injury, stroke, trigeminal neuralgia, etc.), conditions that include a lack of awareness, conditions that include a lack of cognition, neurodegenerative diseases, psychiatric disorders, psychological disorders, obesity disorders, apnea disorders, Autism spectrum disorders, and Alzheimer's disease.

As used herein, the term "neuro-recording modality" can refer to a recording modality that can record time series data corresponding to biosignals (e.g., electrical potentials) emitted from, or associated with, one or more regions of the brain. In some instances, the neuro-recording modality can include two or more recording channels (e.g., corresponding to two or more regions of the brain). Examples of recording modalities can include, but are not limited to, electroencephalogram (EEG), magnetoencephlogram (MEG), thermal imaging, and functional magnetic resonance imaging (fMRI).

As used herein, the term "resting period" can refer to a period of time between instances of abnormal brain interactions during which a subject is free of abnormal behavioral symptoms, which are typically associated with abnormal brain interactions. In some instances, the resting period can refer to a period of time that is characterized by normal behavior during which the subject may experience some brain interactions that do not produce visible behavioral symptoms. For example, in epilepsy, the resting period can be referred to as the "interictal period" between seizures. A subject with epilepsy can be seizure-free during the resting period, and yet may exhibit abnormal epileptiform activity (e.g., interictal epileptic spikes).

As used herein, the term "information inflow" can refer to a characteristic of a brain region that reflects the flow of information to the brain region from other brain regions. Information inflow can be based on directional connectivity between the brain region and at least one other brain region.

As used herein, the term "average information inflow" can refer to the information inflow to certain brain region that is averaged over a certain time period.

As used herein, the terms "directed connectivity" and/or "directional connectivity" can refer to an estimate of functional connectivity between a brain region and at least one other brain region. In one example, directional connectivity can be derived from time series signals, recorded from a neuro-recording modality from multiple brain regions, via multivariate autoregressive modeling of the time series signals. In another example, directional connectivity can be derived from a time series signal that contains activity from a plurality of brain regions and is recorded from a neuro-recording modality, via multivariate autoregressive modeling of the time series signal.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "subject" and "patient" can be used interchangeably herein.

II. Overview

The present disclosure relates generally to identifying a focal area of abnormal brain interactions and, more particularly to systems and methods that can identify a focal area of abnormal brain interactions from time series data recorded during a resting period. In some instances, the systems and methods described herein can employ a computer-implemented technique that can identify a focal area (e.g., one or more epileptogenic foci) from time series data recorded during a resting period. During the resting period, the focal area can be held in check by feedback circuits in the brain that continuously prevent the focal areas from becoming unstable and producing brain interactions (e.g., epileptic seizures and other epileptiform activities). Due to this control, the focal area can exhibit a high information inflow from the feedback circuits holding it in check. The systems and methods described herein can be used to identify the region (or regions) of the brain with a maximum information inflow during the resting period as the region containing the focal area. As described in more detail below, the present disclosure employs measures of directional connectivity to estimate and quantify the strength of information flow between different brain regions to determine the focal area. The average information inflow to each region can then be used to identify the focal area as the region exhibiting the greatest number of instances of maximum average inflow.

The systems and methods of the present disclosure can provide a technique for identifying a focal area of abnormal brain interaction. Advantageously, the present disclosure can facilitate advances in the diagnosis and treatment of neurological disorders characterized by abnormal brain interactions by, for example: complementing the current clinical practice diagnostic procedures for standard-of-care focus identification; quickly determining patients that may require invasive monitoring; quickly identifying the location of the focal area in patients with drug-resistant neurological disorders; improving the treatment of neurological disorders by better delineating the extent of surgical resection or target for implantable stimulators and drug infusion devices; studying the dynamics of the focal area over time to provide insights into the mechanism of generation of the abnormal brain interactions; developing biomarkers and surrogate markers for the presence of abnormal neural networks in high risk patients who are susceptible of developing a neurological disorder in the future; and creating an outpatient setting for focal area localization from routine tests.

III. Systems

One aspect of the present disclosure can include a system that can identify a focal area of abnormal brain interactions in a subject from time series data recorded during a resting period. Although not wishing to be bound by theory, it is believed that the focal area is held at bay during the resting period by surrounding controlling neuronal networks within the brain. The focal area can be identified from time-series data as the area in the brain with the maximum information inflow during the resting period. Advantageously, this permits the focal area to be identified objectively (e.g., without any subjective bias defining what is abnormal) and without requiring occurrence of the abnormal brain interactions.

Figure 2:
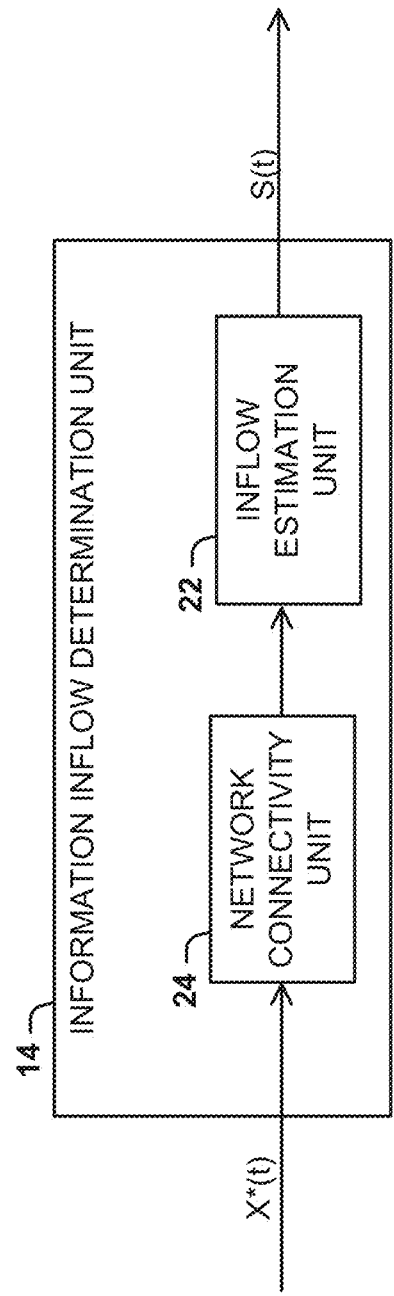
FIG. 2 is a schematic block diagram showing an information inflow determination unit that can be part of the system shown in FIG. 1.
Figure 3:
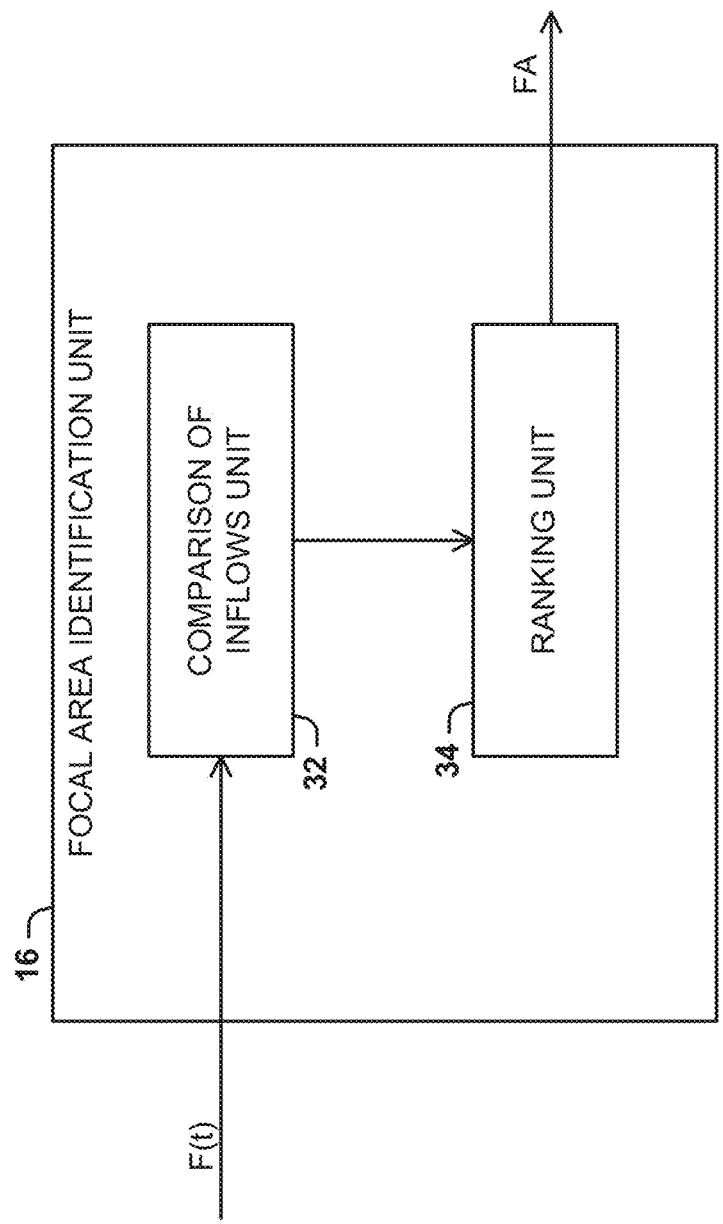
FIG. 3 is a schematic block diagram showing a focal area identification unit that can be part of the system shown in FIG. 1.

FIG. 1 illustrates an example of a system 10 that can identify a focal area (FA), according to an aspect of the present disclosure. FIG. 1, as well as associated FIGS. 2-3, are schematically illustrated as block diagrams with the different blocks representing different components. The functions of one or more of the components can be implemented by computer program instructions. These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the function specified in the block diagrams and associated description.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, the system 10 described herein can be embodied at least in part in hardware and/or in software (including firmware, resident software, micro-code, etc.). Furthermore, aspects of the system 10 can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

As shown in FIG. 1, one aspect of the present disclosure can include a system 10 configured to identify a FA of abnormal brain interactions in a subject. The system 10 can identify the FA in an invasive manner and/or a non-invasive manner during the resting period. As noted above, identification of the FA advantageously can facilitate the development of future diagnostics and treatments (e.g., better targeted treatments) for the abnormal brain interactions.

In one example, the system 10 can be utilized in epileptic patients to identify the epileptogenic focus (e.g., in an invasive manner and/or a non-invasive manner). Identification of the epileptogenic focus can facilitate advances in the diagnosis and treatment of epilepsy by, for example: complementing the current clinical practice diagnostic procedures for standard-of-care focus identification; quickly determining patients that may require invasive monitoring; quickly identifying the location of the epileptogenic focus in patients with drug-resistant focal epilepsies; improving the treatment of epilepsy by better delineating the extent of surgical resection or target for implantable stimulators and drug infusion devices; studying the dynamics of the epileptogenic focus over time to provide insights into the mechanism of epileptogenesis; developing biomarkers and surrogate markers for the presence of epileptogenic networks in high risk patients who are susceptible of developing epilepsy in the future; and creating an outpatient setting for focus localization from routine tests.

The system 10 can include components including at least a receiver 12, an information inflow determination unit 14, and a focal area identification unit 16. One or more of the components can include instructions that are stored in a non-transitory memory 18 and executed by a processor 17. Each of the components can be in a communicative relationship with one or more of the other components, the processor 17, and/or the memory 18 (e.g., via a direct or indirect electrical, electromagnetic, optical, or other type of wired or wireless communication) such that an action from the respective component causes an effect on one or more of the other components.

The receiver 12 can be configured to receive time series data (X(t)) from a plurality of regions in a brain of the subject recorded during a resting period. For example, each of the plurality of regions can correspond to a position of a unique recording electrode and/or a reconstructed source of brain activity. While the time series data (X(t)) recorded during the resting period can include abnormal activity during the resting period (e.g., epileptiform activity), the abnormal activity is not required within the time series signal (X(t)). In other words, the time series data (X(t)) can include normal brain activity. In one example, the time series data (X(t)) can be recorded by a neuro-recording modality that includes a plurality of recording channels (e.g., corresponding to the plurality of regions of the brain) at different places in space (e.g., spatial recording positions).

In some instances, the time series data (X(t)) can be an n-dimensional time series vector representation of different signals corresponding to n different spatial locations:

$$X(t) \rightarrow X_1(t), X_2(t), \ldots, X_n(t))', \qquad \text{Equation 1}$$

where n corresponds to a total number of different spatial locations (corresponding to regions of the brain) where time series signals were recorded, and each vector component $X_i(t)$ denotes the signal recorded at the $i^{th}$ recording site.

The input time series data (X(t)) can include raw time series signals obtained from or generated by a neuro-recording modality. In one example, the neuro-recording modality can be EEG, and the different vector components of the input time series data (X(t)) can correspond to different locations of one or more EEG sensors. In another example, the neuro-recording modality can be MEG, where the receiver 12 can preprocess the raw input time series data (X(t)) into preprocessed time series data (X*(t)). The term "preprocessed time series data (X*(t))" can refer to input to the information inflow determination unit 14 to prevent confusion with the time series data (X(t)) that is input to the receiver 12.

The preprocessed time series data (X*(t)) can include processed signals that are generated from electromagnetic sources in brain regions estimated via the fitting of the raw data X(t) by a brain-source model (e.g., via a type of inverse modeling that may include weighted minimum norm estimates (wMNE), linearly constrained minimum variance (LCMV) beamformers, low resolution electrical tomography (LORETA), etc.). Such a brain-source model can be used to estimate the position and orientation of possible sources (e.g., current dipoles) in the brain that can explain the observed raw signals X(t) over time. For example, the estimates of the position and orientation of such brain-sources can be assigned by three-dimensional MRI images of the subject.

The receiver 12 can provide the time series data (X(t)) and/or the preprocessed data (X*(t)) to an information inflow determination unit 14. For example, the receiver 12 can divide the time series data (X(t)) into a series of time epochs so that the information inflow determination unit 14 can perform its analysis for the different epochs (e.g., each epoch corresponds to a time period in which the maximum information inflow can be determined). The epochs can be non-overlapping or random (e.g., containing one or more overlapping portions). For simplicity of illustration and explanation, the receiver 12 is illustrated as providing the preprocessed data (X*(t)) to the information inflow determination unit 14. Although the preprocessed time series data (X*(t)) is referenced herein, it will be appreciated that the receiver 12 need not perform the preprocessing step and can provide the time series data (X(t)) to the information inflow determination unit 14. The preprocessed time series data (X*(t)) possesses vector properties similar to those as defined for the time series data (X(t)).

The information inflow determination unit 14 can be configured to execute a localization technique on the preprocessed time series data (X*(t)) that is different from traditional FA localization techniques. Traditional techniques process the information outflow from the FA during abnormal brain activity. During a seizure, for example, the epileptic activity starts from the FA and then spreads to other regions of the brain. Such epileptic activity is irregular and unpredictable. In contrast, during the resting period, the FA is held at bay by controlling neuronal networks. Unlike conventional processing techniques, the information inflow determination unit 14 is configured to determine information inflow associated with each of the brain regions (F(t)) based on the preprocessed time series data (X*(t)).

The information inflow associated with a particular brain region can be determined from inflows to the particular brain region from one or more of the other regions of the brain. To shorten the associated processing time, the information inflow associated with a particular region can also be determined from inflows from a portion of the plurality of regions of the brain that is less than all of the regions (e.g., a finite number of neighboring regions to the particular region).

As shown in FIG. 2, the information inflow determination unit 14 can include an inflow estimation unit 22 and a network connectivity unit 24. The inflow estimation unit 22 can be configured to simulate a model representation of the preprocessed time series data (X*(t)). The inflow estimation unit 22 can estimate a model representation of the preprocessed time series data (X*(t)). The model representation can be an autoregressive model that allows the preprocessed time series data (X*(t)). For example, the model representation can be a vector autoregressive model (VAR) or a multivariate autoregressive model (MVAR).

In one example, the autoregressive model VAR(p) can be constructed of an order p (where p is determined based on an autocorrelation of the preprocessed time series data (X*(t)). For example, an autoregressive model can be expressed as:

$$\text{VAR}(p) = \sum_{\tau=1}^{p} B(\tau) X * (t - \tau) + \varepsilon(t), \qquad \text{Equation 2}$$

where $B(\tau)$ represents the n×n coefficient matrices of the model with residuals $\varepsilon(t)$ ideally following a multivariate Gaussian white noise process.

The network connectivity unit 24 can be configured to quantify the network connectivity in the frequency domain based on the model representation of the preprocessed time series data (X*(t)). The network connectivity unit 24 can be configured to quantify the network connectivity (interaction between brain regions) in the frequency domain based on the model representation (e.g., VAR(p)). The term "frequency domain" can refer to the behavior of the biological signal rather than the time period of the recording (e.g., high frequency relates to a rapidly changing signal and low frequency relates to a slowly changing signal). The interaction between brain regions can be estimated by one or more of the following: a directional measure (e.g., capturing the directionality of the flows); a non-directional measure (e.g., not capturing the directionality of the flows); a direct measure (e.g., capturing direct interactions); and/or a non-direct measure (e.g., capturing direct and indirect interactions).

In one example, the network connectivity unit 24 can apply a measure of the generalized partial directional coherence (GPDC) to capture the interactions between the various brain regions. GPDC is a normalized version of partial directional coherence (PDC) that has been used in many applications for the study of brain dynamics. GPDC provides a measure for the direct linear influence of region $X_j$ on region $X_i$ at frequency f conditioned by the rest of the signal variables:

$$GPDCij(f) = \frac{\frac{|Bij(f)|}{\sigma ij}}{\sqrt{\frac{|Bjk(f)|^2}{\sigma^2 kk}}},$$ Equation 3 where $\sigma_{ij}$ is obtained from the covariance matrix of $\epsilon(t)$, $S=[\sigma_{ij}]_{i,\ j=1-n}$, and $B_{ij}(f)$ is the $(i,j)^{th}$ element of the matrix $$B(f) = I - \sum_{\tau=1}^{p} B(\tau)e^{-i2\pi f \tau},$$

where I is the n×n identity matrix.

The network connectivity unit 24 can estimate the average directional connectivity index between nodes (corresponding to information flows for the regions of the brain) based on the quantification of the network connectivity (e.g., from the GPDC) over a given frequency range ($f_1$, $f_2$) Hz. The information inflow to a brain region A from another brain region B can be the portion of information content (e.g., behavior, content, etc.) of the brain region A that is due to or can be explained from its directional connectivity to brain region B. The directional connectivity from brain region B to brain region A can be the estimate of functional connectivity from brain region B to brain region A from appropriate mathematical analysis of the time series signals recorded in regions A and B (e.g., via multivariate autoregressive modeling of the involved time series signals).

The information inflow to a particular region of the brain can be determined by a weighted sum of the information inflows from the rest of the nodes j. For example, assuming a simple sum:

$$InDi = \sum_{j=1, j \neq i}^{n} (GPDCj \rightarrow i(f)).$$ Equation 4

To increase the accuracy associated with the identification of the FA, the statistically significant information inflows (e.g., p<0.05) between the regions can be counted in the determination of information inflow to each region. One way the statistical significance of an information inflow can be evaluated is via a surrogate data scheme. For example, estimation of information inflows from data that is surrogate for real signals for which inter-sample dependencies have been artificially randomized.

The average information inflows for all of the nodes (F(t)) can be provided by the information inflow determination unit 14 to the focal area identification unit 16. The focal area identification unit 16 can be configured to identify the FA of the abnormal brain interactions as one or more of the plurality of regions having a maximum information inflow (e.g., by comparing the information inflow of each of the plurality of regions).

As shown in FIG. 3, the focal area identification unit 16 can include a comparison unit 32 and a ranking unit 34. The comparison unit 32 can compare the value of the information inflow of each of the regions during one or more time periods (e.g., epochs) to determine the region exhibiting a maximum inflow value. The comparison unit 32 can compare the values of information flow by employing a statistical test associated with a property of information inflow (e.g., an outlier detection test). One example of an outlier detection test is a test of Grubb's outliers at a significance level α.

The ranking unit 34 can determine the region most frequently exhibiting a maximum information inflow value (e.g., the first maximum information inflow value, the first two maximum information inflow values, the first three maximum information inflow values, etc.), and identify this region as the FA of abnormal brain activity. For example, the ranking unit 34 can construct a histogram of the information inflow associated with the plurality of regions, and then identify the region with the maximum information flow based on the histogram. The region with the maximum information flow can be identified as the FA. For the identification of the FA, the region of the brain with the maximum information inflow can be estimated over at least a portion of the plurality of brain regions. The identification of the FA can also be based on comparison between ipsilateral and contralateral brain regions to determine the maximum inflow.

IV. Methods

Figure 4:
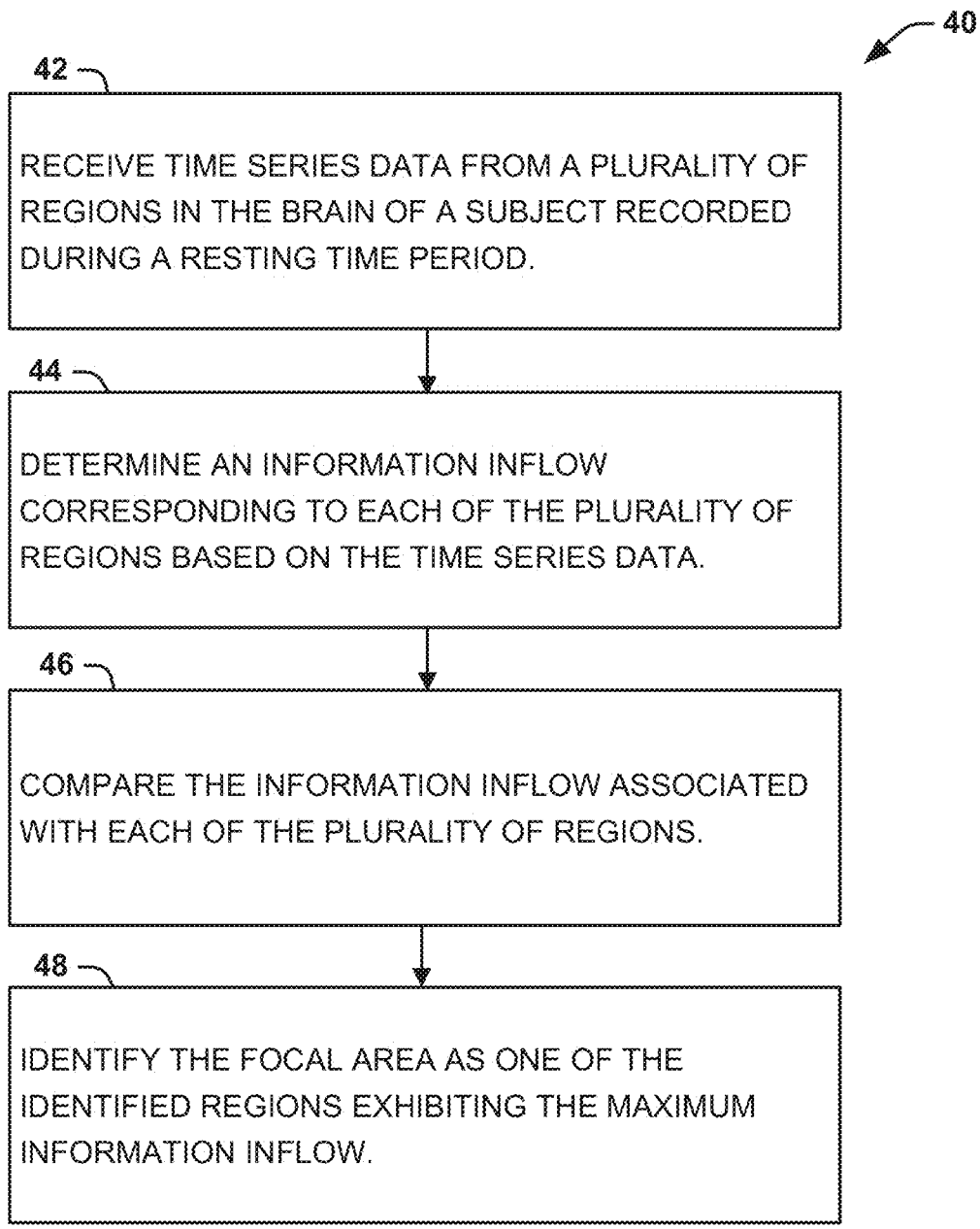
FIG. 4 is a process flow diagram illustrating a method for identifying a focal area of abnormal brain interactions in a subject in accordance with another aspect of the present disclosure.

Another aspect of the present disclosure can include methods that can identify a FA of abnormal brain interactions in a subject from time series data recorded during the resting period. An example of a method 40 that can identify the FA (e.g., invasively and/or non-invasively) is shown in FIG. 4. Another example of a method 50 that can diagnose a neurological disorder in a subject based on the identification of the FA is shown in FIG. 5.

Figure 5:
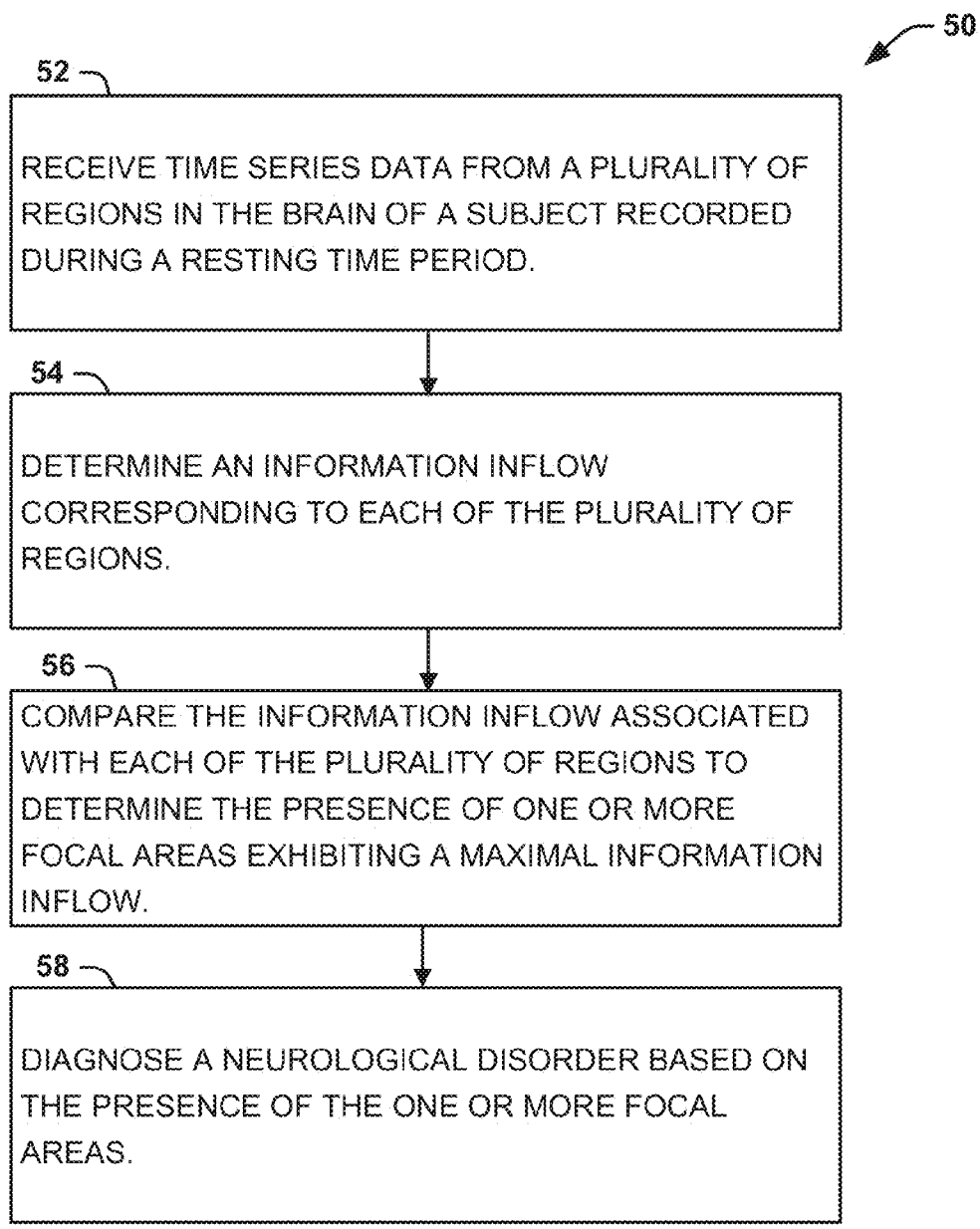
FIG. 5 is a process flow diagram illustrating a method for diagnosing a neurological disorder in a subject in accordance with another aspect of the present disclosure.

The methods 40 and 50 of FIGS. 4 and 5, respectively, are illustrated as process flow diagrams with flowchart illustrations. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 40 and 50 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring to FIG. 4, an aspect of the present disclosure can include a method 40 for identifying a focal area of abnormal brain interactions in a subject from time series data recorded from at least two regions of the brain during a resting period. The time series data can be recorded by a neuro-recording modality (e.g., EEG, MEG, thermal imaging, fMRI, etc.)

At 42, time series data (X(t)) from a plurality of regions in a brain of the subject recorded during a resting period can be received (e.g., by receiver 12). For example, each of the plurality of regions represented by the time series data can correspond to a position of a unique recording electrode and/or a reconstructed source of brain activity. While the time series data (X(t)) recorded during the resting period can include abnormal activity (e.g., epileptiform activity), the abnormal activity is not required within the time series signal (X(t)). In other words, the time series data (X(t)) can include entirely normal brain activity. In some instances, the time series data (X(t)) can be an n-dimensional time series vector representation of different signals corresponding to n different spatial locations (e.g., $X(t) \rightarrow (X_1(t), X_2(t), \ldots, X_n(t))'$). The input time series data (X(t)) can include raw time series signals obtained from or generated by a neuro-recording modality.

At 44, an information inflow corresponding to each of the plurality of regions can be determined (e.g., by inflow estimation unit 22 of information inflow determination unit 14) based on the time series data. The information inflow associated with a particular brain region can be determined from inflows from one or more of the other regions of the brain. To speed up processing time, the information flow associated with a particular region can also be determined from inflows from a portion of the plurality of regions of the brain less than all of the regions (e.g., a finite number of neighboring regions to the particular region).

The information inflow can be determined based on a simulation and/or estimation of a model representation of the time series data (X(t)). The model representation can be an autoregressive model that allows the time series data (X*(t)). For example, the model representation can be a vector autoregressive model (VAR) or a multivariate autoregressive model (MVAR). In an example, the autoregressive model VAR(p) can be constructed of an order p (where p is determined based on an autocorrelation of the time series data (X(t))).

Network connectivity can be quantified based on the model representation of the time series data (X(t)). In one example, a measure of the generalized partial directional coherence (e.g., GPDC that provides a measure of direct linear influence of different regions on one another) can be applied to capture the interactions between the various brain regions. The average directional connectivity index between nodes (corresponding to information flows for the regions of the brain) can be based on the quantification of the network connectivity (e.g., from the GPDC) over a given frequency range $(f_1, f_2)$ Hz.

At 46, the information inflow corresponding to each of the plurality of regions can be compared (e.g., by network connectivity unit 24 of information inflow determination unit 14). The information inflow to a particular region of the brain can be determined by averaging over all of the information inflows from the rest of the nodes. To increase the accuracy associated with the identification of the FA, only the statistically significant information inflows (e.g., $p<0.05$) between the regions can be counted in the determination of information inflow to each region. One way the statistical significance of an information inflow can be evaluated is via a surrogate data scheme. For example, estimation of information inflows from data that is surrogate for real signals for which inter-sample dependencies have been artificially randomized.

At 48, the FA can be identified (e.g., by focal area identification unit 16) as one of the identified regions exhibiting a maximum information inflow. The value of the information inflow of each of the regions during one or more time periods can be compared to values associated with other regions to determine the region exhibiting a maximum inflow value (e.g., based on a statistical test associated with a property of information inflow, such as an outlier detection test). The region most frequently exhibiting the maximum information inflow value can be identified as the FA of abnormal brain interactions (e.g., from a histogram of the information inflow associated with the plurality of regions). For the identification of the FA, the region of the brain with the maximum information inflow can be estimated over all of the plurality of brain regions. The identification of the FA can also be based on comparison between ipsilateral and contralateral brain regions to determine the maximum inflow. Identification of the FA can facilitate the development of diagnostics and treatments for the abnormal brain interactions.

Referring now to FIG. 5, another aspect of the present disclosure can include a method 50 for diagnosing a neurological disorder characterized by one or more focal areas of abnormal brain interactions in a subject. Steps 52-56 are similar to steps 42-48 of the method 40 illustrated in FIG. 4. For example, at 52, time series data can be received (e.g., by receiver 12) from a plurality of regions in the brain of a subject recorded during a resting period. At 54, an information flow can be determined (e.g., by information inflow determination unit 14) corresponding to each of the plurality of regions. At 56, the information flow associated with each of the regions can be compared (e.g., by focal area identification unit 16) to determine the presence of one or more focal areas exhibiting a maximum information flow.

Based on the presence of the FA, at 58, a neurological disorder associated with the abnormal brain interactions can be diagnosed. For example, the diagnosis can be based on a medical standard and/or a comparison to a stored historical data. The diagnosis can, in an example, be based on the location of the focal area and/or a property associated with the maximum information inflow to the region identified as the FA.

V. Examples

The following examples are for the purpose of illustration only and are not intended to limit the scope of the appended claims.

Example 1

This example shows that the interictal focal area identification approach described in connection with the systems and methods above (e.g., based on the measure of GPDC) can localize the epileptogenic focus from raw time series invasive EEG (iEEG) data recorded intracranially during interictal periods without the presence of any epileptiform activity (e.g., epileptic spikes or high frequency oscillations) in the data.

Methods
Subject Selection

The EEG recordings used for the time series data correspond to the resting period of long-term intracranial EEG recordings (phase II) from 3 subjects with focal temporal lobe epilepsy (characteristics presented in Table 1 below).

TABLE 1

Subject Clinical Data

| Subject | iEEG recording duration (hours) | Age | Gender | Clinically assessed focus |
|---|---|---|---|---|
| 1 | 334 | 19 | M | RTD |
| 2 | 18 | 38 | F | LTD |
| 3 | 156 | 25 | M | LTD |

Recording sites were in the left and right hippocampus (LTD, RTD; 6 electrodes each), left and right sub-temporal cortex (LST, RST; 4 electrodes each) and left and right orbitofrontal cortex (LOF, ROF; 4 electrodes each). Seizure epochs were excluded from the time series data.

Focal Area Identification

Let $X(t)=(X_1(t), \ldots, X_n(t))'$ be an n-dimensional time series vector representation of recorded EEG signals at n brain sites, with each vector component $X_i(t)$ denoting the signal recorded at the $i^{th}$ recording site. A vector autoregressive model VARM(p) of order p for X can be constructed as:

$$VAR(p) = \sum_{\tau=1}^{p} B(\tau) X * (t - \tau) + \varepsilon(t), \quad \text{Equation 5}$$

where $B(\tau)$ represents the n×n coefficient matrices of the model with the residuals $\epsilon(t)$ ideally following a multivariate Gaussian white noise process.

The GPDC that measures the direct effect of component process j to i at frequency f is defined as:

$$GPDCij(f) = \frac{\frac{|Bij(f)|}{\sigma ij}}{\sqrt{\frac{|Bjk(f)|^2}{\sigma^2 kk}}} \quad \text{Equation 6}$$

where $\sigma_{ij}$ is obtained from the covariance matrix of $\epsilon(t)$, $S=[\sigma_{ij}]_{i,\,j=1-n}$, and $B_{ij}(f)$ is the $(i,j)^{th}$ element of the matrix $B(f)=I-\Sigma^p_{\tau=1}B(\tau)e^{-i2\pi f\tau}$, where I is the n×n identity matrix.

GPDC provides a measure for the direct linear influence of $X_j$ on $X_i$ at frequency f, conditioned on the rest of the signal variables. In the application of the GPDC measure to brain dynamics, the brain is treated as a network of bi-directionally connected nodes, each one corresponding to a recording site. The EEG is divided into non-overlapping epochs of T seconds in duration and the GPDC functions are estimated within each epoch. The average GPDC over a given frequency range $(f_1,f_2)$ Hz is estimated and denoted by $(GPDC_{j\rightarrow i}(f))_{f\in[f_1,f_2]}$. This quantity is the "directional connectivity index" between nodes. Finally, the inflow at a node/site i is estimated by averaging over all inflows towards i from the rest of the nodes j as $\Sigma_{j=1, j\neq 1}^{n}(GPDC_{j\rightarrow i}(f))$ and the site with the highest inflow within a T-sec epoch is found.

By repeating the procedure for all available epochs, a histogram of the percentage of time that each site is found to have the highest inflow is constructed. Using Grubbs' test for outliers at a significance level α we detect the sites with the highest inflow compared to the rest of the sites over the period of recording.

Results

Figure 6:
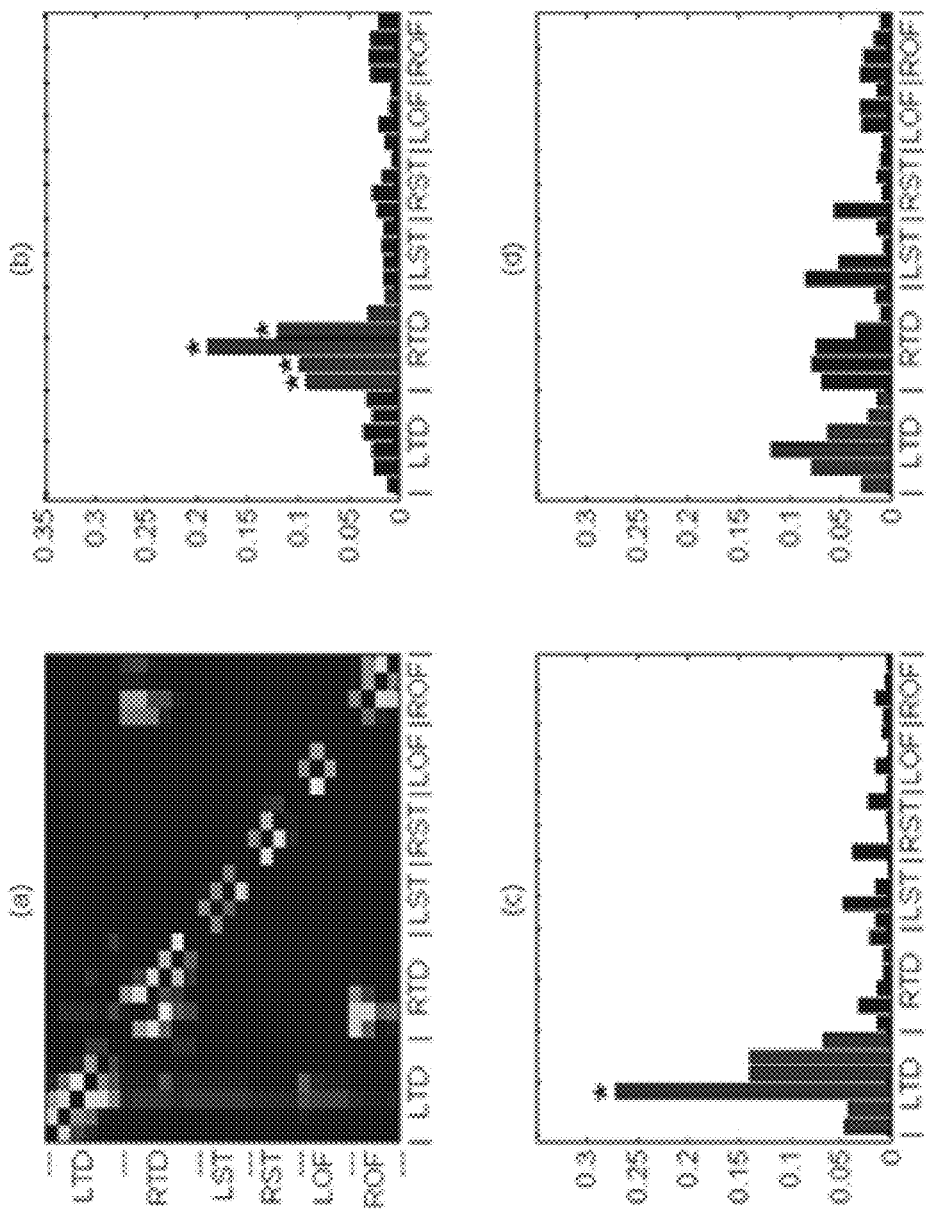
FIG. 6 shows an example of epileptogenic focus localization results using the technique for identification of a focal area from interictal iEEG data obtained from three subjects with temporal lobe epilepsy.

The results of the application of the interictal focal area identification approach using iEEG data for the three subjects with focal temporal lobe epilepsy are presented in FIG. 6. Values of p=7 and T=10 sec were used for estimation of GPDC, in agreement with ones used in the past for the analysis of brain dynamics. The frequency range selected was 0.1-50 Hz and for the outlier test, α was set to 0.01.

In FIG. 6, panel (a) shows the full directional connectivity indices for subject 1. There are strong connections within the right hippocampus (RTD; focus) and moderate connections between the right hippocampus and the right orbitofrontal cortex (ROF). Panels (b)-(d) show the percentage of time each of the brain sites has the highest inflow of information. In 2 out of the 3 subjects (e.g., panels b and c of FIG. 6), the detected focal sites by the interictal focal area identification approach were within the clinically assessed focal region. In the third subject, as shown in panel d, no brain site had statistically significant larger inflow than the rest at the α=0.01 level, even though a clinically assessed focal site (LTD3) did exhibit the largest information inflow. It is interesting to also note that for this subject 3, although the majority of his clinical seizures (6 out of 7) originated from LTD, most of the subclinical seizures (14 out of 16) originated from RTD.

Example 2

This example shows that the interictal focal area identification approach described in connection with the systems and methods above (e.g., based on the measure of GPDC) can localize the epileptogenic focus from short term (1 hour) non-invasive MEG data in connection with a subject's MRI.

Methods
Subject Selection

Continuous MEG recordings from two subjects with neocortical epilepsy and non-lesional MRI (characteristics presented in Table 2 below) were used for this study.

TABLE 2

Subject Clinical Data

| Subject (gender, age) | MRI | Clinical MEG Localization | Gender | Clinically assessed focus | Pathology |
|---|---|---|---|---|---|
| P1 (M, 25) | Negative | Concordant (C) | M | RBT | Gliosis |
| P2 (F, 41) | Negative | Discordant (D) | F | RF | FCD |

MEG Recording

MEG was recorded using a 306 channel Elekta vectorview system which consists of 204 planogradiometers and 102 magnetometer channels. MEG data were band-pass filtered between 1 Hz and 30 Hz using a third order Butterworth digital filter to reduce low frequency drifts. Estimation of the Forward (Lead Field) and Inverse Matrices was performed using the Brainstorm Toolbox of Matlab. One thousand dipoles were uniformly placed within the cortex for creating the forward and inverse matrices.

Focal Area Identification

Figure 7:
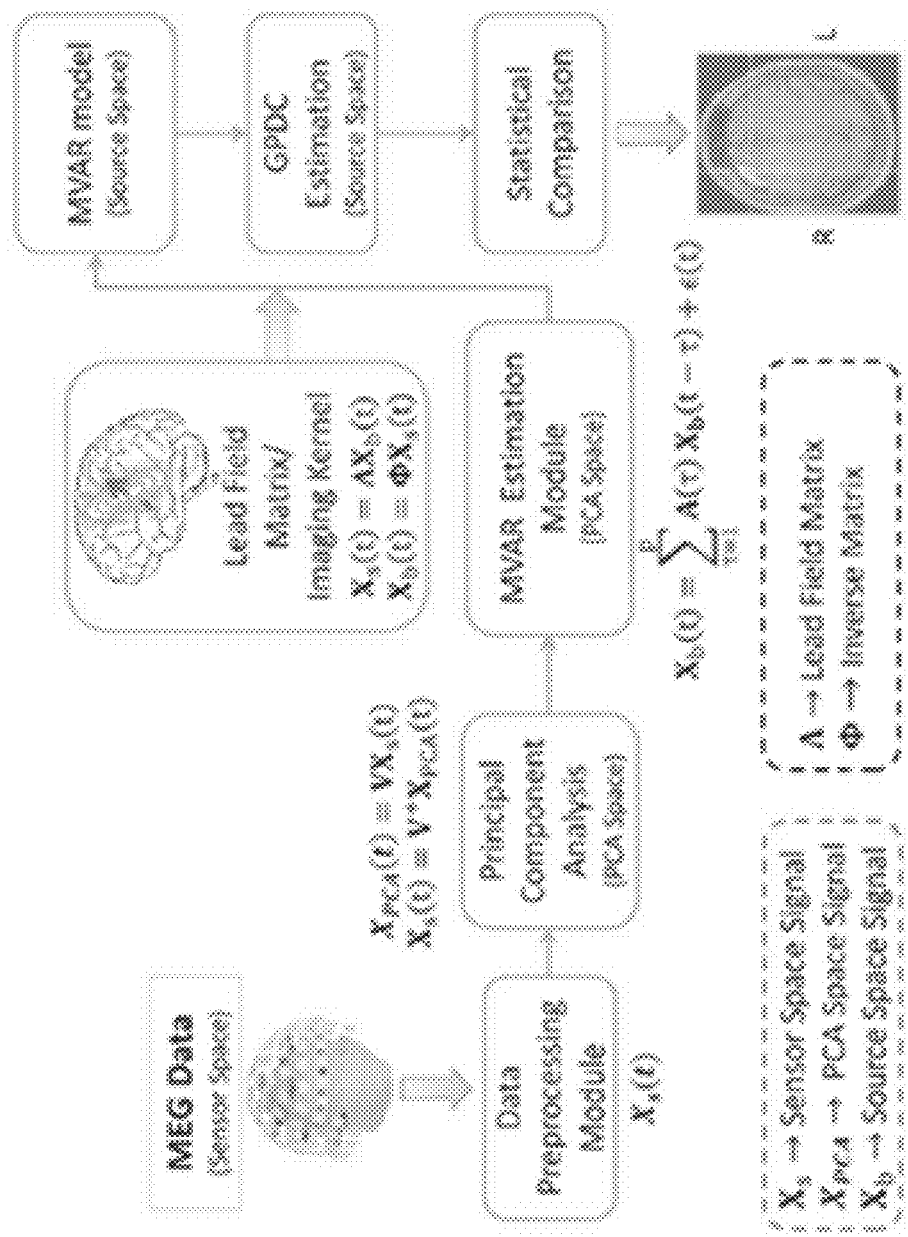
FIG. 7 shows example steps of the technique used in connection with interictal MEG data.

An example process for identification of the focal area is shown in FIG. 7. A VAR model (VAR(p)=$\Sigma^{p}_{\tau=1} B(\tau) X(t-\tau) + \epsilon(t)$) is estimated in the sensor (gradiometer space) and then is projected to the source space. If $X_s(t)$ is the column vector of MEG signals recorded from the gradiometer sensors and $X_b(t)$ the column vector of source signals inside the brain, the following relationships hold for every time point t:

$$X_s(t) = \Lambda X_b(t), \quad \text{Equation 7}$$

$$X_b(t) = \Phi X_s(t) \quad \text{Equation 8}$$

with $\Lambda$ being the lead field matrix or forward operator and $\Phi$ the inverse operator.

The spatial proximity of MEG sensors introduces colinearity between the sensor time series, which can lead to inaccurate estimation of the VAR model. To counteract this, principal component analysis (PCA) is applied on the MEG sensor data and the PCA components that explain 99% of the data variance are selected. Then, the signals $X_{PCA}(t)$ in the reduced space can be written as:

$$X_{PCA}(t) = V X_s(t), \quad \text{Equation 9}$$

$$X_s(t) = V^+ X_{PCA}(t), \quad \text{Equation 10}$$

where V is the mapping matrix of feature vectors from the signals in the sensor space to the reduced PCA space and $V^+$ is its Moore-Penrose pseudoinverse. The VAR(p) model in the PCA space can be estimated as, $$X_{PCA}(t) = \Sigma_{\tau=1}^{p} A(t) X_{PCA}(t-\tau) + \eta(t). \quad \text{Equation 11}$$

Accordingly, using Equations 7-11, the VAR(p) model in the source space can be expressed as:

$$X_b(t) = \Sigma_{\tau=1}^{p} \Phi V^+ A(t) V \Lambda X_b(t-\tau) + \Phi V^+ \eta(t) \quad \text{Equation 12}$$

The directional connectivity measures can now be estimated on the source space directly. The measure of Generalized Partial Directional Coherence (GPDC) is used to estimate the directional information flow between individual brain sources. The average inflow to a given source across a given frequency band at time point t is then estimated. It was assumed that a candidate focal source at time t is the source that exhibits maximum average inflow.

Results

Figure 8:
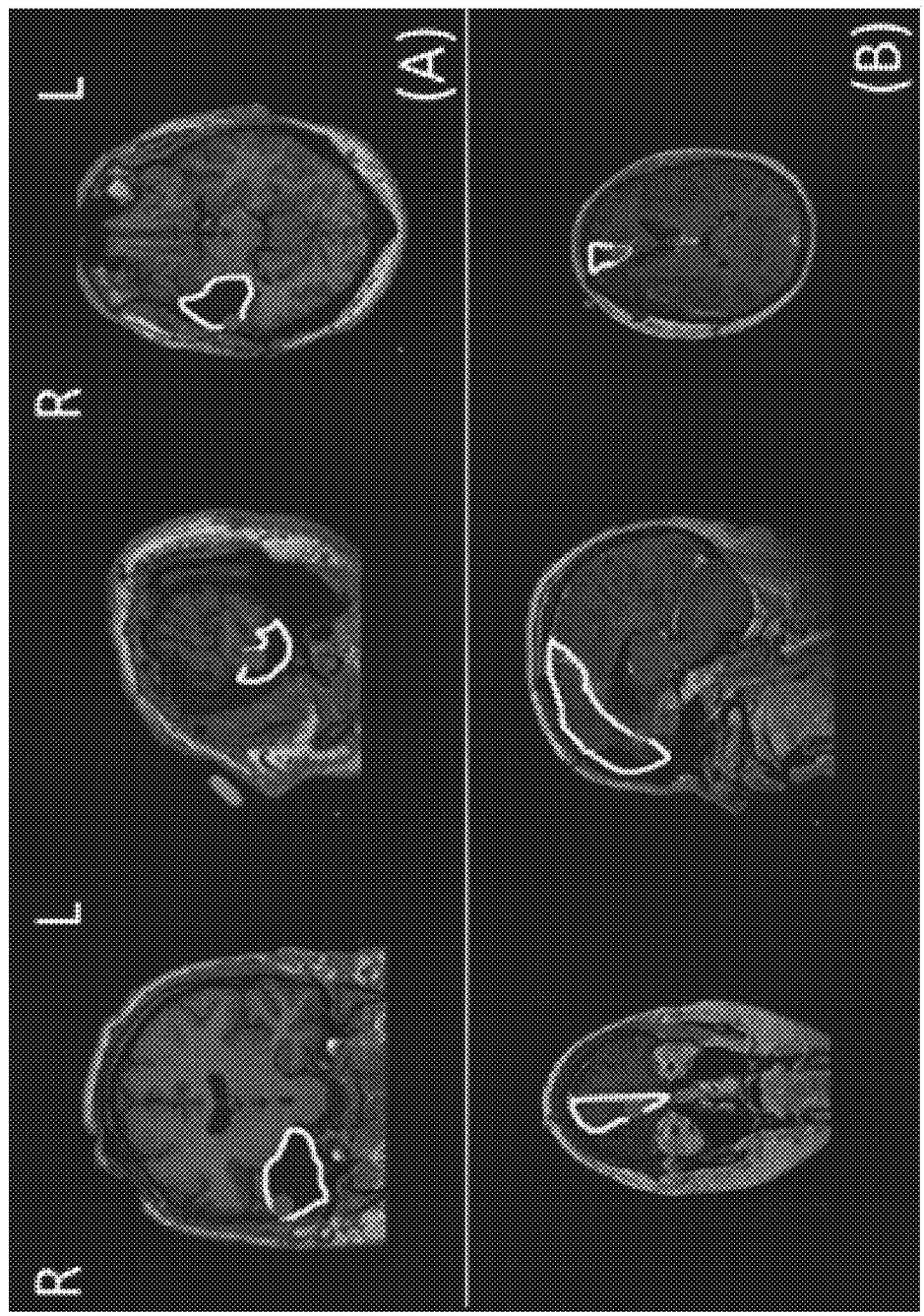
FIG. 8 shows example results of epileptogenic focus localization using the technique for non-invasive identification of a focal area from interictal MEG data superimposed on post-operative MRI images.

The lead field matrix was estimated using the overlapping sphere model and the inverse matrix was estimated using wMNE. The results of the application of the interictal focal area identification approach using MEG data superimposed on MRI images are shown in FIG. 8. The focus can be successfully in both subjects: the derived focal source is within the region of resection (concordant) and subjects became seizure-free, even if traditional clinical MEG analysis around epileptic spikes failed to localize the focus correctly (discordant) in one of the two subjects.

Example 3

This example shows that the interictal focal area identification approach described in connection with the systems and methods above (e.g., based on the measure of GPDC) can localize the epileptogenic focus from short term (1 hour) non-invasive MEG data in connection with a subject's MRI.

Methods

Subject Selection

MEG recordings from five representative patients undergoing MEG as part of their pre-surgical evaluation were analyzed. Each patient represented a special case in terms of the success/failure of the utilized modality for focus localization.

TABLE 3

Subject Clinical Data

| Patient info | Clinical Localization | MRI | SECD Localization | FLA Localization | Seizure Freedom (months) | Pathology |
|---|---|---|---|---|---|---|
| P1 (54 M) | Right Prefrontal Cortex | L | C | C | 57 | FCD |
| P2 (34 M) | Right Frontal Operculum | N | C | C | 51 | FCD |
| P3 (48 M) | Left Inferior Frontal Sulcus | L | C | C | N/A | N/A |
| P4 (42 F) | Right Superior & Middle Frontal Gyri | N | D | C | 26 | FCD |
| P5 (64 M) | Right Peri-Rolandic Cortex (Epilepsia Partialis Continua) | L | I | C | N/A | N/A |

L—Lesional
N— Normal
C—Concordant,
D—Discordant
I—Indeterminate
FCD—Focal Cortical Dysplasia MEG Recording MEG was recorded with a 306-channel whole-head MEG system (Elekta, Sweden) with a sampling frequency of 1,000 Hz and acquisition filtering from 0.1 Hz to 333 Hz. All MEG data were post-processed using a temporally-extended signal space separation (tSSS) algorithm, which also corrects for minor head movements in the MEG array. The processed MEG data were further filtered using a Butterworth filter (a zero phase digital filter was realized) with passband edges at 1 Hz and 30 Hz and downsampled to 200 Hz. As part of the patients' clinical evaluation, source localization analysis with standard Single Equivalent Current Dipole (SECD) was performed using Neuromag's XFIT software (Elekta, Stockholm, Sweden). The location, orientation, and strength of the dipole sources that best fit the measured magnetic fields were calculated based on the SECD model. SECD analysis was performed on data segments containing epileptiform discharges with dipole modeling just before or at the peak of the global field power of each interictal activity (one or several clusters of dipoles, one dipole per spike).

Focal Area Identification

Using the example process for identification of the focal area as shown in FIG. 7, a multivariable autoregressive (MVAR) model is estimated in the sensor (gradiometer space) and then is projected to the source space. The spatial proximity of MEG sensors introduces colinearity between the sensor time series, which can lead to inaccurate estimation of the MVAR model. To counteract this, principal component analysis (PCA) is applied on the MEG sensor data and the PCA components that explain 99% of the data variance are selected. The MVAR model constructed in PCA space is then projected to the source space using lead field and inverse matrix.

One thousand dipoles uniformly distributed over the cortex were used to create the forward and inverse model. The overlapping sphere approach is used to estimate the forward model and weighted minimum norm estimate (wMNE) to create the imaging kernel. Empty room recording was used to estimate the noise covariance matrix. To determine directional connectivity between the assumed dipoles for a 10 second epoch of the recorded MEG data, we estimate the Generalized Partial Directional Coherence (GPDC) between the dipoles and using the projected MVAR model in the source space.

MEG data segments with interictal abnormalities were not removed during the processing. Typical duration of MEG recordings is T=60 minutes. The average information flows of the 10 seconds GPDC between a pair of dipoles over the entire duration of MEG recording are estimated across frequencies 0.1 to 30 Hz. For each dipole, the average local inflow from neighbor dipoles located within the 3-dimensional sphere of radius 5.5 cm and the dipole as the center.

To quantify the presence of abnormal connectivity, the average inflow of each dipole is compared to the one at the corresponding dipole on the contralateral hemisphere based on an unpaired t-test between the inflow values of the 60 closest neighbors of the dipole (including the dipole) and its counterpart in the contralateral hemisphere. The inflow values of dipoles with statistically significant inflow ($p<0.01$) compared to the ones of dipoles in homologous regions of source space within the contralateral hemisphere were further considered in the analysis, while the remaining (non-significant) inflow values were set to zero. The algorithm was implemented in Matlab 2012b (MathWorks, Natick, Mass.). The head model and inverse source model were constructed for each patient using the freely available MEG toolbox Brainstorm.

Results

Patient 1

A 54 year-old right-handed male with a history of medically intractable focal motor seizures starting at the age of 11 years. He presented with daily seizures that were preceded by a "pulling sensation" over the left arm followed by asymmetric tonic stiffening of both arms with preserved awareness, and rare secondarily generalized seizures. Neurological examination was normal. During a period of 5 days of scalp Video-EEG recordings (Nihon-Kohden, Tokyo, Japan) no interictal epileptiform abnormalities were identified. Ictal patterns showed paroxysmal fast activities involving the right parasagittal electrodes (maximum amplitude C4>P4, and Cz>Pz). MRI suggested the presence of a focal malformation within the right hemisphere. This potentially epileptogenic lesion was located anterior to the precentral sulcus extending deep into the white matter. Clinical MEG revealed a single dense cluster of dipoles with uniform orientation located within the right inferior frontal sulcus and anterior to the precentral sulcus. In the multidisciplinary patient management conference (PMC), a decision was made to proceed to intracranial EEG (ICEEG) monitoring to map the extent of the epileptogenic cortex and its relationship to eloquent (motor) areas. Subdural grid electrodes were placed over the frontoparietal convexity focusing on the perirolandic cortex and the lateral, basal and mesial compartments of the frontal lobe. Furthermore, depth electrodes were implanted in the vicinity of the lesion. ICEEG evaluation demonstrated a localized focus within the right inferior frontal sulcus involving the inferolateral and basal frontal regions and extending to the face motor area, as shown in FIG. 9A.

Limited (sublobar) resection of these regions sparing the hand motor area (post-operative MRI shown in FIG. 9D) was undertaken 4 years ago based on results of noninvasive and ICEEG data. The patient has remained seizure-free since.

Figure 9:
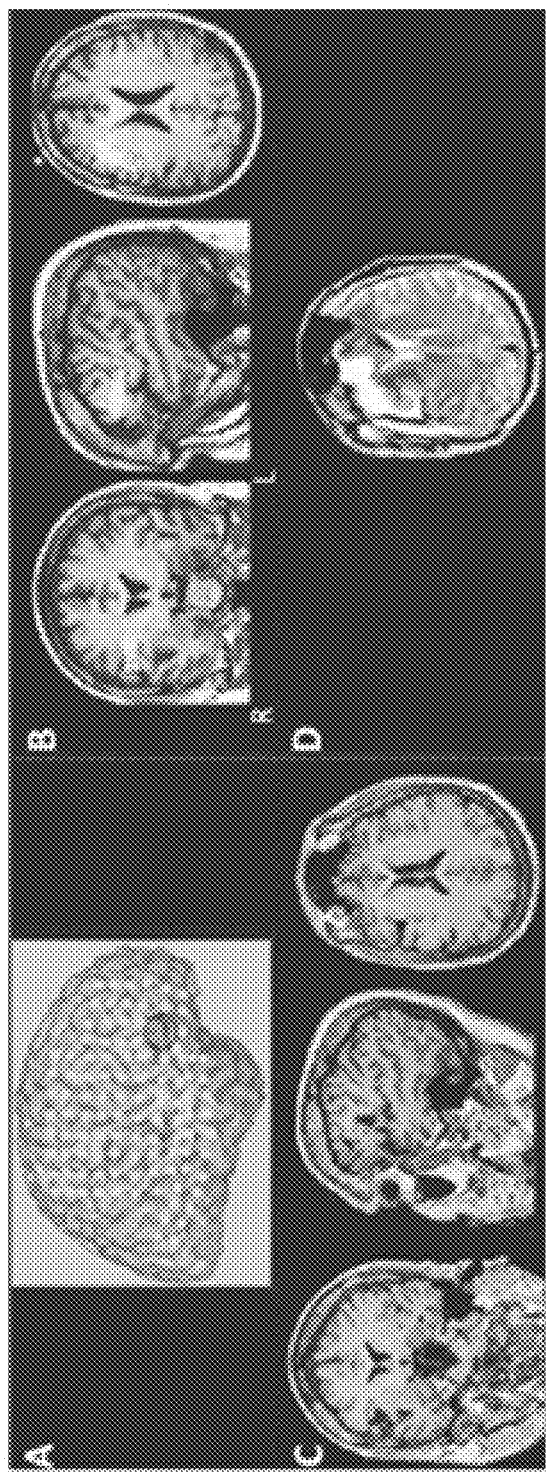
FIGS. 9-13 show example concordant results of clinical evaluation and epileptogenic focus localization using the technique for non-invasive identification of a focal area for various patients.

FIG. 9 shows the results of ICEEG, SECD clinical MEG analysis, retrospective FLA analysis, and area of resection for this patient. Results of SECD and FLA analyses were co-registered to the pre-operative MRI as shown in FIGS. 9 B and C respectively. Both SECD and FLA localized the epileptogenic region to the inferior frontal lobe anterior to the frontal operculum. A second adjacent region of high information flow was observed by the FLA residing more rostrally within the resected inferior frontal lobe. Both SECD and FLA were concordant with the area of resection. Both regions identified by FLA were resected.

Patient 2

A 34 year-old left-handed male presented with intractable focal epilepsy starting at the age of 12 years. Seizures consisted of an aura described as a tingling sensation deep in the throat, which would spread to the left side of the face, followed by left face pulling and left hand posturing. During this period he would drool and have difficulty speaking without alteration of awareness. Seizures were brief in duration and occurred multiple times per day.

Figure 10:
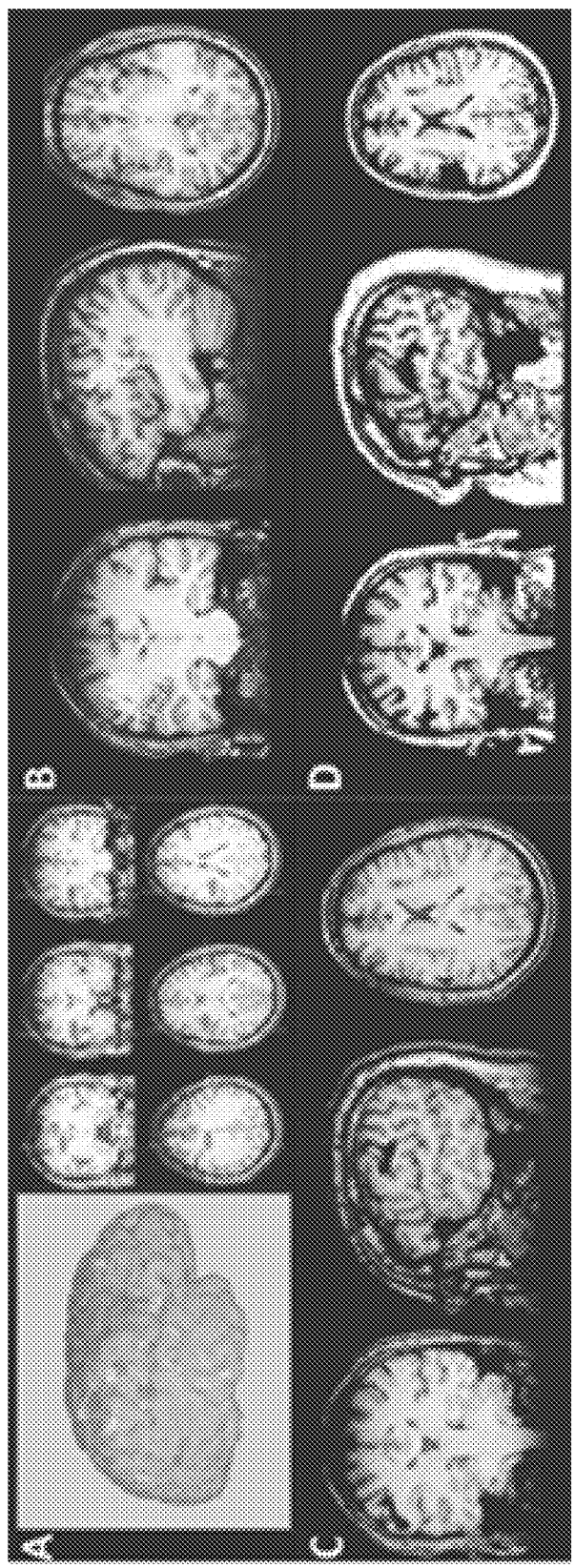

No interictal epileptiform abnormalities were identified during prolonged scalp Video-EEG recordings. Several typical seizures were captured in the epilepsy monitoring unit (EMU). Ictal EEG was non-localizable due to the presence of copious EMG artifacts obscuring any underlying EEG changes. MRI was normal. Interictal PET showed subtle hypometabolism involving the right frontal and temporal operculum. Ictal SPECT did not provide localizing information. Clinical MEG showed a tight cluster of dipoles with uniform orientation located within the right frontoparietal operculum, as shown in FIG. 10B. PMC recommended ICEEG evaluation with stereo-EEG (SEEG) electrodes targeting the right insula, and opercular regions to identify and delineate the seizure onset zone. SEEG showed simultaneous seizure onset from the inferior precentral and parietal opercular regions, as shown in FIG. 10A. The patient underwent limited right frontoparietal opercular resection (FIG. 10D) and has been seizure free for 4 years.

Retrospective FLA analysis localized the region of abnormal inflow near the bottom of the central sulcus and hence had sublobar concordance with the ICEEG-identified seizure onset zone within the fronto-parietal operculum, as shown in FIG. 10C. Both SECD and FLA analyses were concordant with the area of resection.

Patient 3

A 48 year-old left-handed man presented with medically intractable seizures starting at the age of 5 years. Seizures were mostly nocturnal and consisted of complex motor and hyperkinetic behaviors without alteration of awareness occurring in clusters up to 4 per night. Post-ictally he was unable to talk but aware of his surroundings.

Prolonged interictal video-EEG recordings showed spikes involving the left fronto-central region (maximum over the F3>C3 electrodes). Most of the seizures recorded in the EMU were nonlocalizable due to EMG artifacts. Few seizures showed increased slowing and sharp wave activities in the left fronto-central region. MRI showed an area of T2/FLAIR hyperintensity residing within the left inferior frontal sulcus associated with subtle blurring of the gray-white matter junction raising suspicion for an underlying focal cortical dysplasia. Ictal SPECT revealed areas of hyperperfusion in the left inferior frontal and anterior insular regions. Interictal PET showed widespread cortical hypometabolism within the left hemisphere more pronounced in the left inferolateral frontal and adjacent insular regions. Clinical MEG revealed very frequent interictal spikes and polyspikes which were MEG-unique, i.e., they had no identifiable EEG correlate during concurrent scalp EEG recordings. ICEEG evaluation was performed with a combination of depth electrodes targeting the inferior frontal sulcus and anterior insula, and subdural electrodes covering the inferior fronto-parietal region, as well as the basal frontal and anterior temporal neocortex. Interictal spikes and seizures were recorded from the banks of the inferior frontal sulcus corresponding to the clinical MEG and MRI findings, as shown in FIGS. 11A and B.

Functional mapping using cortical stimulation revealed eloquent cortex (Broca's area) in close proximity to the ictal onset zone. Hence, surgical resection of epileptogenic tissue was not recommended for this patient.

Figure 11:
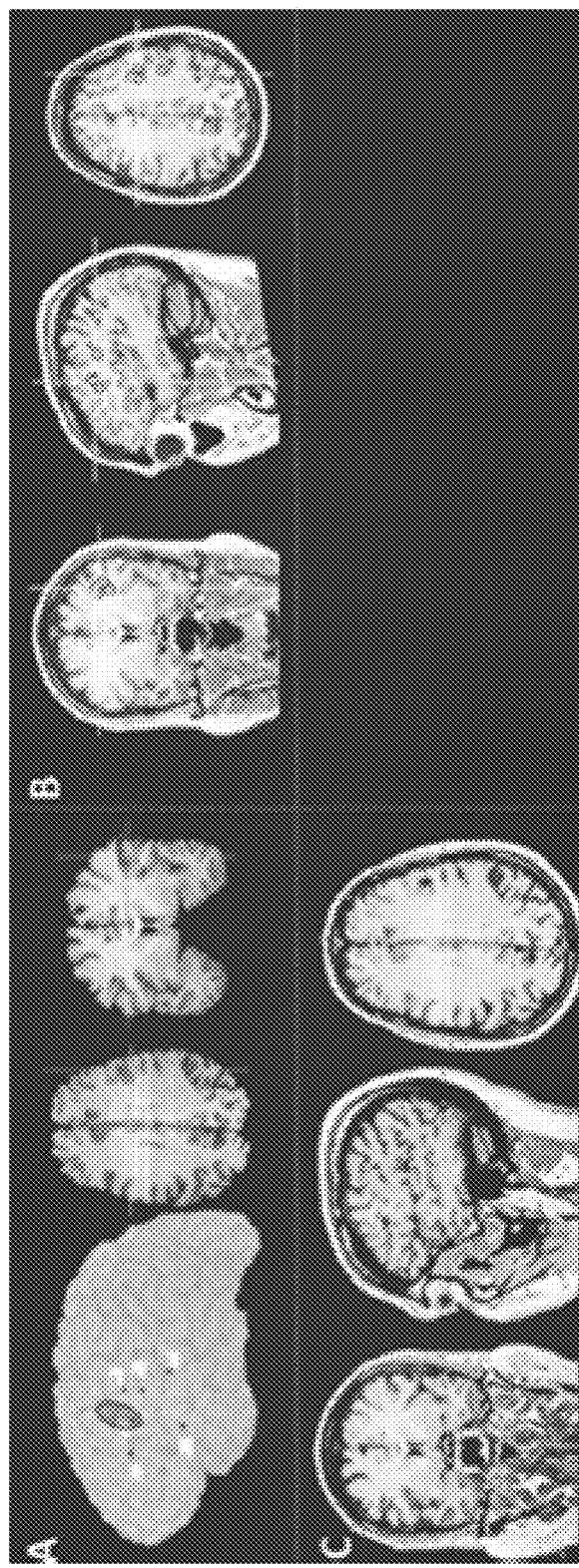

FIG. 11B shows results of SECD analysis, which localized the source of interictal discharges to the inferior and middle frontal gyri surrounding the inferior frontal sulcus. FIG. 11C shows the results of FLA analysis coregistered to the patient's preoperative MRI. Abnormal inflow is observed in the inferior frontal gyrus and is consistent with the concordant findings of ICEEG, MEG and MRI lesion.

Patient 4

A 42 year-old right handed female presented with intractable right frontal lobe epilepsy. Seizures started at the age of 12 years. Seizures were characterized by twitching of the left fingers with loss of consciousness lasting for 1-2 minutes followed by post-ictal confusion and garbled speech. These spells occurred on a daily basis and evolved to secondarily generalized convulsive seizures at least once a week.

Figure 12:
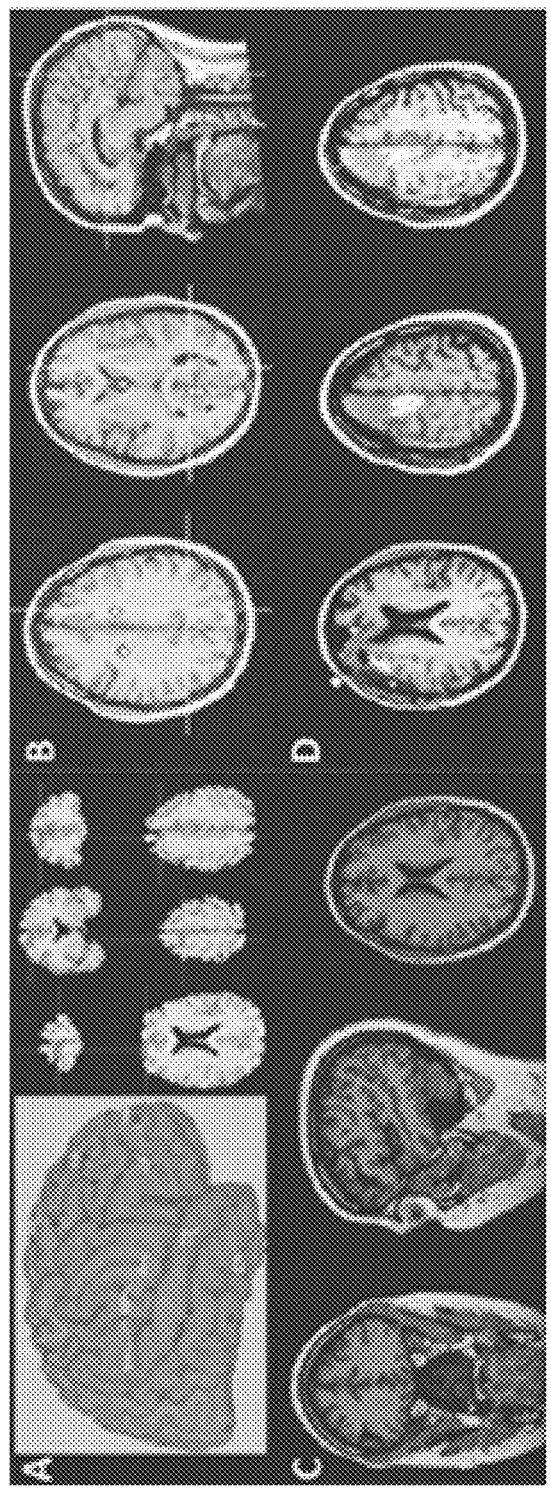

Scalp Video-EEG showed right frontal spikes/polyspikes (maximum over F4-FZ) as well as bifrontal and generalized discharges. Ictal EEG patterns were preceded by a sharp wave with maximum negativity at F4, followed by bifrontal delta slowing. Brain MRI was normal. Ictal-SPECT revealed areas of hyper-perfusion within the left and right posterior insulae. Interictal FDG-PET showed diffuse global cortical hypometabolism and bitemporal hypometabolism without definite asymmetry. Clinical MEG did not provide localizing results due to the widespread distribution of recorded interictal discharges. Nonetheless some of the scalp EEG findings raised suspicion of frontal lobe epilepsy possibly arising from the right hemisphere with rapid secondary bilateral synchrony. Bilateral implantation with stereo-EEG electrodes was recommended to further explore this hypothesis. Depth electrodes were implanted targeting the right and left superior and middle frontal gyri including the supplementary motor area, right and left cingulate gyri and fronto-parietal opercular regions along with both frontal poles. ICEEG demonstrated that seizures were arising from the right anteromesial frontal lobe involving the right superior and middle frontal gyri with rapid (within less than 0.5 seconds) propagation to the contralateral frontal lobe, as shown in FIG. 12A. A right premotor frontal lobectomy was performed (FIG. 12D). The patient has been seizure free for 2 years.

Retrospective FLA analysis revealed region of maximum inflow near the middle frontal gyrus which was concordant with the area of resection, as shown in FIG. 12C. SECD failed to localize the bulk of the patient's widespread interictal activities. Few of the more restricted discharges were falsely localized within the left cingulate gyrus or within the bi-occipital cortex based on SECD findings. None of these regions were included in the area of resection, as shown in FIG. 12B.

Patient 5

A 64 year-old right handed male presented with right peri-rolandic epilepsy starting at the age of 62 years. Discrete focal motor seizures associated with left hand stiffening and jerking lasting for 1-2 minutes with occasional secondary generalization were reported early on. When the patient was referred for video-EEG evaluation he had developed a clinical picture of chronic epilepsia partialis continua (EPC), characterized by inability to control the left hand during prolonged periods of recalcitrant myoclonus involving the wrist and fingers.

Figure 13:
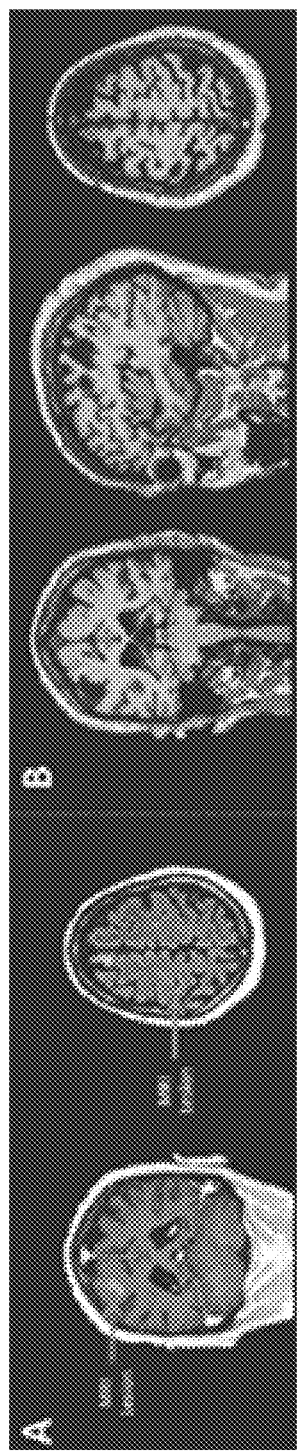

Scalp Video-EEG failed to reveal any interictal or ictal abnormalities during periods of EPC most likely due to the restricted nature of the epileptogenic generator in this patient. Nonetheless the patient exhibited persistent irregular twitches in individual fingers of his left hand, which were present during rest and on action, and could not be stopped by positioning. Brain MRI showed a small area of localized T2 signal alteration within the right central sulcus, as shown in FIG. 13A. Clinical MEG was unremarkable as no epileptic abnormalities were observed during the recording session.

No surgery was recommended for the patient given the localization of the putative MRI lesion within the primary (hand) motor area. He has been maintained on high doses of two antiepileptic medications.

Directional connectivity analysis revealed a region of high inflow within the right pre- and postcentral gyri, as shown in FIG. 13B. Increased inflow was also observed within the right middle frontal gyrus. Even though the scalp video-EEG and clinical MEG studies were unremarkable, the FLA approach produced localizing results which were quite consistent with the patient's typical electroclinical presentation of EPC (arising from a perirolandic epileptogenic generator) and demonstrated sublobar concordance with the location of epileptogenic lesion on MRI.

From the above description, those skilled in the art will perceive improvements, changes and modifications. Such improvements, changes and modifications are within the skill of one in the art and are intended to be covered by the appended claims.

What is claimed is:

1. A system that identifies a focal area of abnormal brain interactions in a subject, the system comprising:
    a non-transitory memory storing computer-executable instructions; and
    a processor that executes the computer-executable instructions to at least:
        receive recordings comprising time series data from a plurality of regions in a brain of the subject recorded during a resting period, wherein the resting period comprises a period of time between instances of abnormal brain interactions during which the subject is free of abnormal behavioral symptoms;
        fit the time series data to a three-dimensional image of the brain of the subject to identify a plurality of possible sources within the plurality of regions of the brain;
        determine an information inflow associated with each of the plurality of possible sources based on the time series data, wherein the information inflow reflects a flow of information to each of the plurality of possible sources from at least one other brain region;
        identify the focal area of the abnormal brain interactions as one of the plurality of possible sources having a maximum information inflow; and
        develop a treatment plan for the abnormal brain interactions in the subject based on the identified focal area.

2. The system of claim 1, wherein the processor executes the computer-executable instructions to determine the information inflow to each possible source by:
    dividing the time series data into a plurality of time epochs;
    for each possible source over each epoch:
        determining a direct linear influence of other regions on the possible source over a corresponding frequency range; and
        determining a value of information inflow to the possible source based on the corresponding directional information inflow and the time series data.

3. The system of claim 2, wherein the processor executes the computer-executable instructions to identify the focal area of the abnormal brain interactions by:
    for each epoch, comparing the value of the information inflow of each of the possible sources to determine a possible source exhibiting a maximum inflow value during the epoch; and
    determining the possible source most frequently exhibiting the maximum information inflow value and identifying this possible source as the focal area of abnormal brain interactions.

4. The system of claim 3, wherein the comparison step is based on a statistical outlier detection test.

5. The system of claim 2, wherein the direct linear influence is determined according to an estimation of interactions between each of the plurality of possible sources.

6. The system of claim 2, wherein the direct linear influence is used to determine a network connectivity between the plurality of possible sources that contributes to the determination of the value of the information inflow to each of the plurality of possible sources.

7. The system of claim 1, wherein the focal area of abnormal brain interactions is associated with at least one of an epileptic seizure, a paroxysmal neurological disorder, a stroke, an autism spectrum disorder, a psychological disorder, a traumatic brain injury, an obesity disorder, an apnea disorder, a condition comprising a lack of awareness, and a neurodegenerative disease.

8. The system of claim 1, wherein the time series data comprises at least one of electroencephalogram data, magnetoencephalogram data, thermal imaging data, and functional magnetic resonance imaging data.

9. A method for identifying a focal area of abnormal brain interactions in a subject, the method comprising the steps of:
    receiving, by a system comprising a processor, recordings comprising time series data from a plurality of regions in a brain of the subject recorded during a resting period, wherein the resting period comprises a period of time between instances of abnormal brain interactions during which the subject is free of abnormal behavioral symptoms;
    fitting, by the system, the time series data to a three-dimensional image of the brain of the subject to identify a plurality of possible sources within the plurality of regions of the brain;
    determining, by the system, an information inflow corresponding to each of the plurality of possible sources based on the time series data, wherein the information inflow reflects a flow of information to each of the plurality of possible sources from at least one other brain region;
    comparing, by the system, the information inflow corresponding to each of the plurality of possible sources;
    identifying, by the system, the focal area as one of the possible sources exhibiting a maximum information inflow; and
    developing a treatment plan for the abnormal brain interactions in the subject based on the identified focal area.

10. The method of claim 9, further comprising determining a statistical significance of the information inflows corresponding to each of the plurality of potential sources, wherein the identifying is based on the information inflows determined to be statistically significant.

11. The method of claim 9, wherein the treatment plan comprises at least one of a surgical plan, an infusion pump placement, and a stimulating electrode placement based on the identified focal area.

12. The method of claim 9, wherein each of the potential sources corresponds to at least one of a position of a different recording electrode or a reconstructed source of brain activity.

13. The method of claim 9, wherein the comparing step is based on a statistical test associated with a property of the information inflow.

14. The method of claim 9, wherein the determining step further comprises:
    determining a network connectivity between the plurality of potential sources; and
    determining of the value of the information inflow to each of the plurality of potential sources based on the network connectivity.

15. A method for diagnosing a neurological disorder characterized by one or more focal areas of abnormal brain interactions in a subject, the method comprising the steps of:

receiving, by a system comprising a processor, recordings comprising time series data from a plurality of regions in the brain of the subject recorded during a resting period, wherein the resting period comprises a period of time between instances of abnormal brain interactions during which the subject is free of abnormal behavioral symptoms;

fitting, by the system, the time series data to a three-dimensional image of the brain of the subject to identify a plurality of possible sources within the plurality of regions of the brain;

determining, by the system, an information inflow corresponding to each of the plurality of possible sources based on the time series data, wherein the information inflow reflects a flow of information to each of the plurality of possible sources from at least one other brain region;

comparing, by the system, the information inflow associated with each of the plurality of possible sources to determine the presence of one or more focal areas exhibiting a maximum information inflow;

diagnosing, by the system, the neurological disorder based on the presence of one or more focal areas; and developing, by the system, a treatment plan for the diagnosed neurological disorder based on the presence of one or more focal areas.

16. The method of claim 15, further comprising the steps of:

constructing, by the system, a histogram of the information inflow associated with the plurality of potential sources; and determining, by the system, the maximum information inflow based on the histogram.

17. The method of claim 15, wherein the information inflow corresponding to each of the potential sources is determined based on a directional information inflow estimation and a network connectivity assessment.

* * * * *